United States Patent [19]

Ehrenfeld et al.

[11] Patent Number: 5,610,029
[45] Date of Patent: Mar. 11, 1997

[54] MEDIUM FOR DETECTING TARGET MICROBES IN A SAMPLE

[75] Inventors: Elizabeth Ehrenfeld, Falmouth, Me.; Colin Fricker, Reading, Great Britain; David E. Townsend, Scarborough, Me.

[73] Assignee: Idexx Laboratories, Inc., Westbrook, Me.

[21] Appl. No.: 423,134

[22] Filed: Apr. 18, 1995

Related U.S. Application Data

[63] Continuation-in-part of Ser. No. 334,788, Nov. 4, 1994, abandoned.
[51] Int. Cl.$^6$ .............................. C12Q 1/04; C12Q 1/02; C12Q 1/10; G01N 33/48
[52] U.S. Cl. .................... 435/34; 435/29; 435/4; 435/38; 436/63; 436/166; 436/172
[58] Field of Search ................... 435/34, 29, 4, 435/38; 436/63, 166, 172

[56] References Cited

U.S. PATENT DOCUMENTS

| | | | |
|---|---|---|---|
| 3,206,317 | 9/1965 | Golber | 435/34 |
| 3,496,066 | 2/1970 | Berger | 435/34 |
| 4,129,483 | 12/1978 | Bochner . | |
| 4,235,964 | 11/1980 | Bochner | 435/34 |
| 4,591,554 | 5/1986 | Komura et al. | 435/34 |
| 4,925,789 | 5/1990 | Edberg | 435/34 |
| 5,393,662 | 2/1995 | Roth et al. | 435/34 |
| 5,429,933 | 7/1995 | Edberg | 435/34 |

FOREIGN PATENT DOCUMENTS

| | | |
|---|---|---|
| 0254771 | 12/1986 | European Pat. Off. . |
| 0261931 | 3/1988 | European Pat. Off. . |
| 0332752 | 9/1989 | European Pat. Off. . |
| 0451775 | 10/1991 | European Pat. Off. . |
| 0574977 | 12/1993 | European Pat. Off. . |
| 9118111 | 11/1991 | WIPO . |
| 9212259 | 7/1992 | WIPO . |
| 9420638 | 9/1994 | WIPO . |

OTHER PUBLICATIONS

Berg et al., "Rapid Detection of Total and Fecal Coliforms in Water by Enzymatic Hydrolysis of 4–Methylumbelliferone–β–D–Galactoside," *Applied and Environmental Microbiology* 54:2118–2112 (1988).

Brenner et al., "New Medium for the Simultaneous Detection of Total Coliforms and *Escherichia coli* in Water," *Applied and Environmental Microbiology* 59:3534–3544 (1993).

Damare et al., "Simplified Direct Plating Method for Enhanced Recovery of *Escherichia coli* on Food," *J. Food Science* 50:1736–1738 (1985).

de Man, "The Probability of Most Probable Numbers," *European J. Appl. Microbiol.* 1:67–78 (1975).

Jay, *Modern Food Microbiology*, 4th ed., pp. 113–121 (1992).

Kilian and Bulow, "Rapid Identification of *Enterobacteriaceae*," *Acta Path. Microbiol. Scand. Section B* 87:271–276 (1979).

Peeler et al, "Chapter 6—The Most Probable Number Technique," *Compendium of Methods for the Microbiological Examination of Foods*, 3rd ed., pp. 105–120, Vanderzant and Splittstoesser eds., American Public Health Association (1992).

*Standard Methods for the Examination of Water and Waste Water*, 18th ed., Greenberg et al. eds, pp. 9–45 to 9–64 (1992).

Thomas, "Bacterial Densities From Fermentation Tube Tests," *J. Am. Water Works Assoc.* 34:572–576 (1942).

Sarhan and Foster, "A rapid fluorogenic method for the detection of *Escherichia coli* by the production of β–glucuronidase," *J. Applied Bacteriology* 70:394–400 (1991).

*Primary Examiner*—Gary E. Hollinden
*Assistant Examiner*—Louise Leary
*Attorney, Agent, or Firm*—Lyon & Lyon

[57] ABSTRACT

The invention features a medium for the detection of target microbes in a liquified environmental or biological sample in less than 18 hours.

27 Claims, No Drawings

MEDIUM FOR DETECTING TARGET MICROBES IN A SAMPLE

This application is a continuation-in-part of Ehrenfeld et al., U.S. Ser. No. 08/334,788, filed Nov. 4, 1994, now abandoned entitled "Medium For Detecting Target Microbes in a Sample" hereby incorporated by reference herein.

FIELD OF THE INVENTION

This invention is in the field of chemistry, biology and microbiology and relates to novel means for detecting the presence of target microbes in a sample of a possibly contaminated material.

BACKGROUND

Microorganisms are present ubiquitously in biological specimens and environmental media suitable for their growth. However, some prove harmful to higher organisms and means for detecting their presence is important to preserve the public health. Many means for detecting various types of microorganisms are available offering various advantages with respect to speed and specificity.

All microorganisms have certain requirements for growth and reproduction. In general, microorganisms require the presence of the following for growth: an energy source such as light or carbon compounds; and a source of raw materials including carbon, nitrogen, sulfur, and phosphorus as well as trace amounts of other minerals. Further, microorganisms must be present in a suitable environment wherein an appropriate temperature, pH, salinity and oxygen concentration is maintained.

A common procedure used to detect the presence of microorganisms involves adding a specimen to a culture medium containing all the necessary elements to support growth. The sample may be natural or pretreated, as by membrane filtration, before being added to the culture medium. The medium may or may not contain chemicals such as antimicrobial agents or antibiotics which suppress the growth of microorganisms other than the target microorganism. Usually, these culture media are sterilized to assure no interference from contaminating microbes, and a rather long incubation period of from twenty-four to forty-eight hours is usually required to grow the microbes to detectable concentrations. Additionally, once growth is detected in these procedures, the target microorganism must be identified using one or more tests specific for a variety of physical or biochemical characteristics unique to the target microbes. These procedures are, therefore, labor intensive and time consuming.

Efforts have been made to simplify and expedite the detection process. Among these efforts have been attempts to measure specific metabolic by-products of individual microorganisms. These methods include: electrical impedance assays, ATP assays, antibody-based assays and carbon-14 labelled substrate assays. Indicators of microbial growth have also been used to monitor growth of target microbes which change color only after growth of the target microbe is detected. These indicators normally react chemically with a metabolic by-product produced by the target microbes resulting in a color change in the medium. Examples of chemicals which change color in the presence of pH changes associated with growth include phenol red, bromocresol blue, and neutral red. For example, Golber, U.S. Pat. No. 3,206,317 uses phenol red, a chemical which changes color in the presence of acidic waste products produced by the target microbe. Berger et al., U.S. Pat. No. 3,496,066 describes the use of compounds which bacteria convert to dyestuffs, e.g., tropinones and dioxans, Bochner, U.S. Pat. No. 4,129,483 describes using a non-biodegradable substance (tetrazolium) which is chemically reduced to produce a color change. In all of these examples, the indicator is a compound which does not serve as a source of a required nutrient.

Edberg, U.S. Pat. No. 4,925,789 describes the use of a nutrient indicator which not only serves as a nutrient source, but also changes color upon being metabolized. The patent, herein incorporated by reference, provides a medium containing a nutrient indicator which, when metabolized by a target bacterium, releases a moiety which imparts a color or other detectable change to the medium. The procedure takes advantage of an enzyme specificity unique to a particular species or groups of bacteria. It suggests using antibiotics to select for growth of the microorganisms targeted and provides specific examples of liquid based assays. Other methods previously used such as Kilian et al., *Acta. Path. Microbiol. Scand.* Sect.B §7 271–276 (1979) and Damare et al., *J. Food Science* 50:1736 (1985) report use of agar-based media without antibiotics.

SUMMARY OF THE INVENTION

The present invention features a medium which allows detection of the presence or absence of a target microbe in a liquified environmental or biological sample within as little as 18 to 24 hours. For example, *Escherichia coli* and other coliforms may be detected within about 18 hours from the start of the incubation period with great specificity. Thus, the present medium is distinct from prior media in which about 24 hours are required to obtain a test result for *E. coli*. Such a medium can be made using varying amounts of both nutrients and growth indicators. However, the invention provides amino acid, vitamin and element ingredients in amounts greater than those previously used. Other features of the media of this invention include the use of sodium pyruvate to assist the recovery of metabolically injured bacteria, the use of a thermo-equilibration period, the use of less sodium chloride, and the provision of other metabolites in suitable amounts.

The medium contains an effective amount of vitamins, amino acids, trace elements and salts operable to support viability and reproduction of the target microbe in the presence of a nutrient indicator. Media which have proven optimal in this invention for the detection of total coliforms and *E. coli* in a sample include a source of ammonium ions (e.g., at a final sample concentration of about 4.5 to 5.5 g/liter ammonium sulfate), a buffer (e.g., about 6.0 to 7.5 g/liter HEPES free acid, and 4.7 to 5.8 g/liter HEPES sodium salt), about 0.13 to 0.16 g/liter D-gluconic acid, a source of sulfite (e.g., about 0.036 to 0.044 g/liter sodium sulfite), an antifungal agent (e.g., about 0.0009 to 0.0011 g/liter amphotericin B), a source of magnesium ions (e.g., about 0.09 to 0.11 g/liter magnesium sulfate), a nutrient indicator (e.g., about 0.450 to 0.550 g/liter ortho-nitrophenyl-β-D-galactopyranoside (ONPG) and about 0.067 to 0.085 g/liter 4-methylumbelliferyl-β-D-glucuronide (MUG)), a source of zinc ions (e.g., about 0.00045 to 0.00055 g/liter zinc sulfate), and a source of manganese ions (e.g., about 0.00045 to 0.00055 g/liter manganese sulfate).

In addition, the following components are provided in the following minimum amounts. The maximum or optimal amounts of each ingredient may be several fold (e.g., 3–10 or even 20 fold) greater than those provided below. Specifically, such a medium will have a total nitrogen content of at least about 1.1 to 1.7 g/liter. Amino acids required for growth of the target microbe are provided. Not all amino acids must be provided and the relative amount of each can vary. Those in the art will recognize that natural sources of such amino acids can be used rather than pure sources. Amino acids may be provided from a variety of sources. Normally, only essential amino acids which cannot be synthesized endogenously by the target microbes must be provided. These can be provided from natural sources (e.g., extracts of whole organisms) as mixtures or in purified form. The natural mixtures may contain varying amounts of such amino acids and vitamins (see below). For general guidance, specific amounts of such amino acids and vitamins are indicated below. These amounts are for guidance only and are not limiting in this invention. Those in the art will recognize that many different combinations of amino acids and vitamins can be used in media of this invention. The lists provided below exemplify just one such example. Amino acid contents preferably include at least the following in amounts of at least about the amounts indicated: Alanine (0.025 g/liter), Arginine (0.03 g/liter), Aspartic Acid (0.056 g/liter), Glutamic Acid (0.1 g/liter), Glycine (0.015 g/liter), Proline (0.09 g/liter), Cystine (0.002 g/liter), Histidine (0.006 g/liter), Isoleucine (0.01 g/liter), Leucine (0.03 g/liter), Lysine (0.03 g/liter), Methionine (0.01 g/liter), Phenylalanine (0.018 g/liter), Serine (0.029 g/liter), Threonine (0.018 g/liter), Tryptophan (0.003 g/liter), Tyrosine (0.0064 g/liter), and Valine (0.023 g/liter).

Other inorganic compounds may be included to aid in the growth of the target microbe. These include the following (to the extent not already provided in the above sources of various chemical entities): Iron (e.g., at least about 0.00165 µg/l), Calcium (e.g., at least about 0.0003 g/liter), Phosphate (e.g., at least about 0.1 g/liter), Potassium (e.g., at least about 0.007 g/liter, preferably about 0.05 g/liter), Sodium (e.g., at least about 0.03 g/liter), and trace amounts of Cobalt, Copper, Lead, Magnesium, Manganese, Chloride, Tin, and Zinc.

Vitamins required by the target microbe for growth may also be provided. These can be provided in a pure form or as part of a more complex medium. Such vitamins may be present in at least the following amounts: Biotin (0.00005 mg/l), Cyanocobalamin (trace), Choline (0.05 mg/l), Inositol (0.060 mg/l), Nicotinic Acid (0.014 mg/l), Niacin (0.00385 mg/l), PABA (0.02 mg/l), Folic Acid (0.000075 mg/l), Pantothenic Acid (0.01095 mg/l), Pyridoxine (0.0015 mg/l), Riboflavin (0.0028 mg/l), Thiamine (0.0037 mg/l), and Thymidine (0.010 mg/l).

Those in the art will recognize that organic carbon, nitrogen, trace elements, vitamins and amino acids can be provided in many forms. Generally, it is preferred to have an amount of vitamins and amino acids at least as great as those specific amounts provided above, but those in the art will recognize that the actual concentration of each ingredient may be varied so that reduction in the amount of one ingredient can be compensated by an increase in the amount of another. This is particularly relevant when the growth requirement of a particular target microbe is known. Some ingredients may be provided in reduced amounts or deleted if they are synthesized endogenously by the target microorganism. Most preferably the total amount of such ingredients is greatly in excess of the total amount provided in the above example. Amounts on the order of five to ten times those described above are particularly effective in allowing detection of microorganisms within a short period of time (18 hours) while maintaining detection specificity.

Other ingredients of such a medium include antibiotics active against gram positive non-target microbes, antibiotics active against gram negative non-target microbes, inducers of the enzyme(s) which catalyze the metabolism of the nutrient indicator(s), DNA precursors, amino acid precursors, and supplemental sources of potassium and phosphorus.

The nutrient indicator is present in the medium in an amount which is sufficient to support growth of the target microbe until a detectable characteristic signal is produced in the medium during growth. Together, the vitamin, amino acid, trace element, salt, and nutrient-indicator ingredients allow sufficient growth of the target microbe so that a detectable change in the sample may be observed in less than about 24 hours. The nutrient indicator alters a detectable characteristic of the sample only when it is metabolized by the target microbe. Therefore, it may be used to confirm the presence or absence of a microbe in the sample. The nutrient indicator must only be metabolized by the target microbe in the medium. If other microbes are present in the sample which could metabolize the nutrient indicator then their growth must be suppressed by use of specific antibiotics. In addition, while it is preferred that the nutrient indicator is the only source of the specific type of nutrient for the target microbe, the medium may contain other such sources, but in amounts that will not reduce the specificity of the medium. For example, the nutrient indicator may be the only source of carbon for the target microbe. Alternatively, other carbon sources may be present (e.g., amino acids) which are not preferentially used by the target microbe. If desired, some small amount of another carbon source may be present which might be preferentially used by the target microbe, but the amount provided is such as not to reduce the specificity of the medium over one without such a carbon source.

The term "target microbe" means one or more microbes whose presence or absence is to be determined. The term may refer to a single microbe (e.g., *Escherichia coli, Enterococcus faecalis, Staphylococcus aureus, Mycobacterium fortuitum,* and *Klebsiella pneumonia*), a genus of microbes, a number of related species of microbes (e.g., coliforms), or an even larger group of microbes having a common characteristic (e.g., all gram-negative bacteria). The invention contemplates designing the medium and method to take advantage of unique enzyme specificities or other characteristics unique to different groups, families or species of microbes. Thus, the nutrient indicator may vary depending upon which microbe is selected as the target. However, it is not intended that the term "target microbe" include all microbes.

The term "18 hours" means the time required for about 95% of the liquid samples containing only about one to ten coliform per 100 ml to display a detectable characteristic change. The temperature, amount and type of enzyme inducer present, amount of nutrients provided in the medium, and the relative health of the bacteria all affect the detection time. The amount of nutrients such as amino acids, vitamins and trace elements provided may affect the growth rate of the target microbe, and thus, the detection time. Thermally equilibrating the sample to an incubation temperature of about 35° C. after adding the medium may decrease the time required for detection. The amount of enzyme inducer may also decrease the time to detection. Enzyme inducers found in the medium are agents which act to induce the activity or expression of the enzyme which metabolizes the nutrient indicator. Such inducers include isopropyl-β-D-thiogalactoside (IPTG) which induces β-D- galactosidase activity and ethyl-β-D-thioglucoside which induces β-glucosidase activity. The relative health of the microbe also affects the time required for detection. Adding such agents as pyruvate which may aid recovery of injured organisms may, therefore, speed detection. If large numbers of target microbes are present in the sample (i.e., less than 10 microbes/100 ml sample), more rapid detection is also possible. In this invention, the media provided allows detection of low amounts of target microbes (i.e. less than 10/100 ml) in the 18 to 24 hour time period, at least 95% of the time. Standard methods can be used to determine such ability.

The term "medium" means a solid, powder or liquid mixture which contains all or substantially all of the nutrients necessary to support growth and reproduction of the target microbes. This invention includes both media which are sterilized (i.e., in which no growth results upon incubation of the medium alone, or with a sterile diluent) as well as media which are not sterile.

The term "liquified" means substantially in liquid form, though it is also meant to include pulverized or homogenized samples of solid substances having at least a 10% liquid content. The phrase is meant to exclude a gelled medium, such as is formed with agar.

The terms "environmental" and "biological" mean taken from or coming from a substance capable of supporting one or more life forms, including algae, fungi and bacteria. Examples include but are not limited to recreational waters, marine waters, drinking waters, sewage effluents, and food substances.

The term "inoculation" means at or near the time the liquified environmental or biological sample is mixed with the medium of this invention. It is meant to be the time at which the two substances are substantially mixed together.

The term "effective amount" is an amount within the range which allows or promotes growth and reproduction of a target microorganism within the specified time. That is, an amount which allows microbes to adapt to the medium, synthesize the necessary constituents for reproduction, and subsequently reproduce. It is not meant to be specific and may vary depending upon such factors as the sample size and the concentration of the target microbes. Generally, the term indicates the amount required to detect less than 100 target microbes per 1 ml sample, most preferable less than 100 microbes per 100 ml sample, or even 1 microbe per 100 ml sample.

The terms "vitamins", "amino acids", "trace elements" and "salts" are meant to include all molecules, compounds and substances classified in each category by those of skill in the art whether organic or inorganic, and the categories are not intended to exclude any substance which may be necessary for or conducive to maintaining life.

The term "antibiotic" means a molecule or peptide which prevents or inhibits growth and reproduction of one or more species or groups of non-target microbes. Examples are well known in the art, however, the term is meant to exclude detergents which may specifically or non-specifically inhibit or prevent bacterial growth. Examples of specific antibiotics which may be useful in the invention include colistin, nalidixic acid, and ansiomycin.

The term "nutrient indicator" means a molecule or substance containing a moiety that is a source of an essential nutrient for the target microbe, and a moiety which causes or produces an observable characteristic change in the medium or sample. A nutrient indicator includes nutrient sources attached to or conjugated with chromogens. Nutrient sources may provide essential vitamins, minerals (e.g., phosphate), trace elements, amino acids, or carbohydrate energy source (e.g., lactose). The nutritional requirement of a microorganism increases as the microorganism progresses from the phase in which nutrients are accumulated for reproduction (lag phase) into the phase during which reproduction actually occurs at a relatively rapid rate (log phase). Consequently, nutrient indicators are optimally metabolized during their growth periods which produces a detectable and characteristic change in the sample. Preferably, the nutrient indicator includes a nutrient moiety and a chromogen. Chromogens include any moieties which produce a color change observable in the visible range or fluorescence when properly excited by the proper energy source. Examples include, but are not limited to, orthonitrophenyl, phenolphthalein, and 4-methylumbelliferone moieties. While the nutrient indicator may provide the sole source of an essential nutrient, other sources of such nutrients may be provided, so long as adequate selectivity and sensitivity of the medium is maintained.

The term "detectable characteristic signal" includes any change in a sample which may be detected by one or more of the human senses. The term includes such examples as a color change in the visible or non-visible wavelength ranges, a change in state such as between solid, liquid and gas, an emission of gas, or a change in odor.

In a preferred embodiment, the medium includes sufficient sodium pyruvate to assist the growth of metabolically injured cells. The term "metabolically injured" includes instances where cellular metabolism is altered from the optimal or homeostatic state by an external trauma. Examples of "metabolic injury" include instances of cell exposure to excessive heat, cold, chlorination, or drying conditions.

In another preferred embodiment, the nutrient indicator alters the color of the microbe-specific medium. The color change may be apparent in the visible wavelength range, or it may be fluorescence which is apparent in a visible wavelength range after exposure to an external UV source. The color generally results from the enzymatic release of a chromogenic moiety from the nutrient indicator. This moiety is colored when conjugated to the nutrient portion of the nutrient indicator, and is colorless when in unconjugated form (that is, when it is no longer conjugated to, or bound to, the nutrient moiety). Examples of chromogenic moieties that may be conjugated to a nutrient moiety include, but are not limited to orthonitrophenyl moieties which produce a yellow color when released from the nutrient-indicator, phenolphthalein moieties which produce a red color when released from the nutrient-indicator, 4-methylumbelliferone moieties which become fluorescent when excited at about 366 nm when released from the nutrient-indicator, and bromo-chloro-indole moieties which become blue when released from the nutrient-indicator.

The term "microbe-specific medium" means a medium which allows substantial growth of only the target microbe. This includes media which contain one or more antibiotics specific for inhibiting growth of microorganisms other than the target microbe, and it includes media which alternatively or additionally contain one or more nutrient indicators which are preferably not metabolized by microorganisms other than the target microbe to any substantial degree. The term "substantial" as used in this context, means that the medium still allows specific (i.e., at least 95% or even 98% accurate) and sensitive (i.e., at least 95% or even 98% detection levels) detection of the target microbe, as measured by standard procedures.

In yet another preferred embodiment, the microbe is a coliform bacterium or more specifically the target microbe is

*Escherichia coli*. Other preferred embodiments involve the choice of the nutrient indicator. In one preferred embodiment, the nutrient indicator is a β-D-glucuronidase substrate, examples of which include orthonitrophenyl-β-D-glucuronide, β-naphthalamide-β-D-glucuronide, α-naphthol-β-D-glucuronide, and 4-methylumbelliferyl-β-D-glucuronide. Alternatively, the nutrient indicator is a β-D-galactosidase substrate, examples of which include orthonitrophenyl-β-D-galactopyranoside and 4-methylumbelliferyl-β-D-galactopyranoside. The nutrient indicator may be a β-D-glucosidase substrate, examples of which include orthonitrophenyl-β-D-glucose. In yet another embodiment, the nutrient indicator may be a L-pyronidonyl aminopeptidase substrate, such as orthonitrophenyl-β-L-pyronidonyl, β-naphthalamide-β-L-pyronidonyl, α-naphthol-β-L-pyronidonyl and methylumbelliferyl-β-L-pyronidonyl, or the nutrient indicator may be an L-alanine aminopeptidase substrate, such as L-alanine-β-L-orthonitrophenyl, β-naphthalamide-β-L-alanine, β-naphthol-β-L-alanine, and 4-methylumbelliferyl-β-L-alanine.

The term "coliform" means any of a group of non-spore forming gram negative, oxidase negative rod-shaped bacteria which display β-galactosidase activity and normally inhabit the gastrointestinal tract of humans. The group includes *Klebsiella pneumonia* and *Escherichia coli* whose presence in water is understood by those in the art to be presumptive evidence of fecal contamination, as well as *Enterobacter cloacae, Citrobacter freundii*, and *Serratia plymuthica*.

Preferably, the medium also contains one or more antibiotics which prevent microbes other than the target microbe from metabolizing the nutrient indicator. That is, the medium contains antibiotics which are specific inhibitors of growth of microbes other than the target microbe, and effectively prevent growth of at least some of those microbes. Most preferably, these antibiotics operate against one or more gram-positive and gram negative non-coliform bacteria. Examples of such antimicrobials which may be useful against other bacteria and yeast include coilstin, nalidixic acid, ansiomycin, and amphotericin-B.

Another feature of the invention is a method for detecting the presence or absence of a target microbe in an environmental or biological liquid sample, preferably including the step of warming the sample to incubation temperature in a liquid incubator after adding the microbe-specific medium. Most preferably, the incubation temperature is about 35° C. The term "liquid incubator" means a liquid warmed to a specified temperature or temperature range. This may include any form of water bath for instance. Such an incubator is advantageous over previously used air incubators, since the medium can reach an optimal incubation temperature faster in a liquid incubator than in an air incubator.

The invention also features a method for detecting the presence or absence of a target microbe in an environmental or biological liquid sample within 24 hours. *Escherichia coli* and other coliforms may be detected using this method within only about 18 hours. This method features first mixing the sample with the medium of the invention, warming the sample and medium mixture to an incubation temperature, preferably 35° C., for about 20 minutes. The sample is then transferred to an air incubator, preferably at 35° C., for about 18 hours. The medium includes an effective amount of vitamins, amino acids, elements, and salts so that coliform microbes can grow and reproduce. Also, the medium includes an effective amount of a nutrient-indicator to support growth of the coliform bacteria and which produces a detectable characteristic signal if metabolized by the target microbe. Next, the sample is monitored to determine whether the detectable characteristic has been altered. Preferably, the medium also contains one or more antibiotics in an amount sufficient to inhibit or prevent growth of non-coliforms that are potentially present in the test sample.

In other embodiments, the invention uses the apparatus described by Naqui et al. in U.S. Ser. No. 08/201,110, filed Feb. 23, 1994 now U.S. Pat. No. 5,518,892 hereby incorporated by reference. The quantifying step involves providing an environmental or biological sample in a liquid form. The sample is placed or dispensed into the sample holding bag described by Naqui et al., and mixed with a medium to allow and promote growth of target bacteria. The mixture is incubated and the quantity and quality of the color change detected. The quantity and quality obtained is compared to a series of samples for which the concentration of bacteria was known.

The invention provides an optimized medium for determining the presence of target microbes. Microbes, e.g., bacteria, grow much faster in this medium than in those currently available as a result of the increased amounts of vitamins and amino acids provided. Therefore, the results of testing are more rapidly available. Rapid results save both money and time in the laboratory. Speed also decreases the threat to the public health allowing early alerts and remedial measures to deal with the presence of some microorganisms in such places as drinking water supplies and recreational waters. Further, the method of this invention generally does not require confirmatory tests since microorganism-specific nutrient-indicators may be used. Additionally, the invention does not require use of a sterile medium.

Other features and advantages of the invention will be apparent from the following description of the preferred embodiments thereof, and from the claims.

BRIEF DESCRIPTION OF THE PREFERRED EMBODIMENTS

In the following description, reference will be made to various methodologies known to those of skill in the chemical, biological and microbiological arts. Publications and other materials setting forth such known methodologies to which reference is made are incorporated herein by reference in their entireties as though set forth in full. The compositions, methods, and products of this invention are applicable to biological and environmental specimens, and are useful in the chemical, biological and microbiological arts for the detection of microorganisms.

Detecting Microorganisms based on enzyme specificity

Specific microorganisms derive their nutrients from an array of sources. However, the ability to metabolize certain sources may be unique to a particular microorganism or group of microorganisms. Families, groups or species of microorganisms may share enzyme specificity for certain nutrients which are lacking in other microorganisms. By taking advantage of the metabolic characteristics of specific microorganisms, it is possible to test for the presence of these enzyme systems, and thus, the microorganisms which display these enzyme systems themselves. See Edberg, supra. Many enzymes have been identified which are specific to particular groups of microorganisms and others likely will be identified in the future.

Gram Negative Bacteria

Gram negative bacteria contain an endotoxin as part of their outer cell membrane. They may contaminate environmental or biological samples as well as pharmaceuticals and other medical preparations. Thus, it is important to have effective screening methods available to determine whether gram negative bacteria are present.

Some gram negative bacteria as a group have L-alanine aminopeptidase enzyme activity. Nutrient indicators such as L-alanine-β-orthonitrophenyl, β-naphthalamide-β-L-alanine, α-naphthol-β-L-alanine, and 4-methylumbelliferyl-β-L-alanine may be used in the medium as nutrient indicators to test for the presence or absence of gram negative bacteria. Antibiotics useful for eliminating all gram positive bacteria from the medium are well known in the art. Thus, it is possible to detect the presence of any gram negative bacteria by using nutrient indicators of L-alanine aminopeptidase activity in a medium containing an antibiotic which eliminates gram positive bacteria.

Enterococcus

The enzyme β-D-glucosidase is found in the enterococcus group of bacteria. The enzyme may catalyze the hydrolysis of appropriate nutrient indicators containing chromogenic or fluorogenic moieties linked to a β-glucoside. This property may be used to indicate the presence or absence of enterococci in a sample. Nutrient indicators such as 4-methylumbelliferyl-β-D-glucopyranoside may be used to indicate the presence of enterococci. The growth of other microorganisms expressing β-D-glucosidase activity may be inhibited by providing a medium containing antibiotics which support the growth of those non-target microorganisms but do not substantially inhibit enterococcus growth. Amikacin sulfate, bacitracin, and amphotericin B are examples of such antibiotics. Additionally, growth of other organisms may be inhibited by providing a growth environment having a high pH of about 9.6 or an elevated temperature of about 45° C. Enterococci can grow at this high pH and elevated temperature allowing specific detection of enterococci under those conditions.

*Staphylococcus aureus*

This species is capable of metabolizing orthonitrophenyl phosphate. Thus, if the growth medium contains this nutrient indicator as the only source of phosphate, *Staphylococcus aureus* will grow while microorganisms not capable of metabolizing orthonitrophenyl phosphate will not. A color change will be produced by the release of the orthonitrophenyl moiety.

*Mycobacterium fortuitum*

This species requires $SO_4$ as its source of sulfur, and this species can metabolize phenolphthalein-sulfate. Thus, in a selective medium whose only sulfur source is phenolphthalein-sulfate, this species will grow and produce a characteristic color change by release of the colored moiety.

*Escherichia coli* detection

The enzyme β-D-glucuronidase is present in *E. coli*. Nutrient indicators such as orthonitrophenyl-β-D-glucuronide, β-naphthalamide-β-D-glucuronide, α-naphthol-β-D-glucuronide or methylumbelliferyl-β-D-glucuronide are examples of nutrient indicators which may be used in a medium for the detection of *E. coli*. The antibiotics vancomycin and ansiomycin may be added to select for *E. coli* from gram positive bacteria and yeast in amounts by weight of about 0.0001% to 0.01%.

Edberg, U.S. Pat. No. 4,925,789 reports on a liquid based bacterial growth medium which allows specific detection of *E. coli* in a sample after about 24 hours of incubation. It has a reported specificity to detect the presence of one CFU (colony forming unit) in 100 ml of volume. However, in contrast to the specific examples in Edberg, the detection of total coliforms including such bacteria as *E. coli* can be obtained in about 18 hours if other media or methods described in this invention are used, and surprisingly a specificity to detect one CFU per 100 ml of volume may still be attained. Specifically, this invention features media which increase the amount of vitamins and amino acids present to facilitate cell growth. For instance, shorter detection times are obtained if the amount of vitamins and amino acids is increased over the amounts featured in the medium described by Edberg. A medium including the following compounds is especially useful for detecting *Escherichia coli* allowing detection within 24 hours due to more rapid growth rate and fine specificity. Providing amounts of Component I at levels of 5 to 10 times those indicated allows detection of *Escherichia coli* within 18 hours.

While specific amino acids and vitamins are noted, as well as some elements, those in the art will recognize, as described above, that the relative amounts of each component can vary significantly, without loss of specificity.

TABLE 1

| COMPONENT I INGREDIENT | SOURCE | AMOUNT | |
|---|---|---|---|
| Nitrogen | | 1.10 to 0.70 | g/l |
| Amino Acids | Alanine | 0.025 to 0.08 | g/l |
| | Arginine | 0.030 to 0.08 | g/l |
| | Aspartic Acid | 0.056 to 0.085 | g/l |
| | Cystine | 0.002 to 0.005 | g/l |
| | Glutamic Acid | 0.102 to 0.207 | g/l |
| | Glycine | 0.015 to 0.15 | g/l |
| | Histidine | 0.005 to 0.020 | g/l |
| | Isoleucine | 0.0145 to 0.046 | g/l |
| | Leucine | 0.030 to 0.079 | g/l |
| | Lysine | 0.034 to 0.068 | g/l |
| | Methionine | 0.011 to 0.023 | g/l |
| | Phenylalanine | 0.018 to 0.037 | g/l |
| | Proline | 0.088 to 0.093 | g/l |
| | Serine | 0.028 to 0.044 | g/l |
| | Threonine | 0.018 to 0.032 | g/l |
| | Tryptophan | 0.0036 to 0.005 | g/l |
| | Tyrosine | 0.0064 to 0.018 | g/l |
| | Valine | 0.023 to 0.056 | g/l |
| Elements | Cobalt | trace | |
| | Copper | trace | |
| | Iron | 0.00165 | mg/l |
| | Lead | trace | |
| Vitamins | Biotin | 0.00005 to 0.00016 | mg/l |
| | Choline | 0.050 to 0.10 | mg/l |
| | Cyanocobalamin | trace | |
| | Folic Acid | 0.000075 to 0.0014 | mg/l |
| | Inositol | 0.060 to 0.12 | mg/l |
| | Niacin | 0.00385 to 0.0070 | mg/l |
| | Nicotinic Acid | 0.014 to 0.03 | mg/l |
| | PABA | 0.020 to 0.038 | mg/l |
| | Pantothenic Acid | 0.01 to 0.013 | mg/l |
| | Pyridoxine | 0.0015 to 0.0021 | mg/l |
| | Riboflavin | 0.0028 to 0.0058 | mg/l |
| | Thiamine | 0.0037 to 0.026 | mg/l |
| | Thymidine | 0.010 to 0.02 | mg/l |
| Enzyme Inducers | | 0.015 | g/l |

| COMPONENT II | Concentration (g/liter)* |
|---|---|
| Ammonium sulfate (anhydrous) | 5.000 |
| HEPES (free acid) | 6.864 |
| HEPES ($Na^+$ salt) | 5.292 |
| D-Gluconic acid (hemicalcium salt) | 0.145 |
| Sodium sulfite (anhydrous) | 0.040 |
| Amphotericin B (solubilized) | $0.0010^A$ |
| Magnesium sulfate (anhydrous) | 0.100 |
| ONPG | 0.500 |
| Methylumbilliferyl-β-D-glucuronide | 0.075 |
| Zinc sulfate (heptahydrate) | 0.0005 |
| Manganese sulfate | 0.0005 |
| Pyruvic acid ($Na^+$ salt) | 0.005 |
| Sodium chloride | 0.100 |
| DNA Precursors | 0.005 |

TABLE 1-continued

| | |
|---|---|
| Gram Positive Antibiotics | 0.005 |
| Gram Negative (non-coliform) Antibiotics | 0.01 |
| Amino Acid Precursors | 0.001 |
| Phosphate sources | 0.1 |

*Trace amounts of elements are optional, and include amounts less than 0.001 g/liter. Trace amounts of vitamins are also optional, and include amounts less than 0.5 µg/g.
^AFinal concentration of Amphotericin B after taking into account the concentration of the solution.

In a more specific example of a medium of this invention, Component I is provided at ten times the amount noted in Table I (±10%) with Component II. this is called herein Medium 2.

Total coliform bacteria

An enzyme-based nutrient indicator detection system has the specificity to detect one coliform bacterium in a 100 ml volume in 18 hours. Total coliforms may be detected by monitoring the medium for the appearance of an intense yellow color in the test medium after 18 hours when orthonitrophenyl-β-D-galactopyranoside (ONPG) is used in the medium as a primary carbohydrate source. The enzyme β-D-galactosidase is found in all coliform bacteria and acts to catalyze the hydrolysis of orthonitrophenyl-β-D-galactopyranoside. This reaction is both non-reversible and extremely sensitive to the presence of coliform bacteria. If E. coli is present among the total coliforms, the medium turns fluorescent blue when an ultraviolet lamp in the range of 366 nm is placed near the test sample. This fluorescence is due to the hydrolysis of 4-methylumbelliferyl-β-D-glucuronide (MUG) to produce the fluorescent compound 4-methylumbelliferone (MU), and the reaction is catalyzed by the enzyme β-D-glucuronidase which is found in over 97% of E. coli strains.

The detection can be achieved with the greatest speed and least cost when the medium is optimized to produce the fastest rate of bacterial growth and enzyme activity. Additionally, sodium pyruvate may be added to the medium to assist the recovery and growth of metabolically injured bacteria. An amount of about 0.0005% by weight is normally sufficient. As well, thermally equilibrating the sample and medium mixture to about 35° C. by placing the sample in a water bath at about 35° C. for 20 minutes before placing in a dry incubator significantly decreases the time required for detection.

Analyzing water for coliforms

It is important to detect the presence of coliform bacteria in drinking water and in recreational waters. If antibacterial agents are present in the water, it may be useful to add neutralizing agents, such as sodium thiosulfate or sodium EDTA. Otherwise, the presence of coliforms may be detected by preparing the sample according to standard techniques. A 100 ml water sample is collected, the growth medium is added to the sample, the sample is incubated at a temperature conducive to bacterial growth (which normally occurs at 35° C.), and the presence of coliforms is indicated by a change in the color of the sample after about 18 hours. A positive result may occur at any time up until 22 hours after mixture of the sample and the medium. It may occur much more rapidly in the presence of a relatively high concentration of coliforms. The presence of one coliform in a 100 ml volume may be determined using the medium and procedure described in this invention.

Chromogenic moieties

Numerous substrates including a chromogenic moiety have been demonstrated to display a characteristic color change in samples containing target microorganisms which exhibit specific enzyme activity. For example, in the presence of β-D-glucuronidase, orthonitrophenyl-β-D-glucuronide produces a color change to yellow, 4-methylumbelliferyl-glucuronide produces fluorescence after excitation at 366 nm, and bromo-chloro-indole-β-D-glucuronide produces a color change to blue when E. coli is present. In the presence of β-D-galactosidase, orthonitrophenyl-β-D-galactopyranoside produces a color change to yellow and 4-methylumbelliferyl-β-D-galactopyranoside produces fluorescence after excitation at 366 nm.

Some combinations have proven effective for detecting the presence of E. coli as well as total coliform bacteria. 4-methylumbelliferyl-β-D-glucuronide may be used together with orthonitrophenyl-β-D-galactopyranoside. If any coliforms are present, the solution changes color to yellow in the visible wavelength range. If both E. coli as well as other coliforms are present, the sample solution both changes color to yellow and fluoresces after excitation at 366 nm.

Nutrient indicators may be produced by methods well known to those of skill in the art. The methods generally feature coupling or conjugating a nutrient moiety to a chromogenic moiety, thereby, producing a nutrient indicator. Examples of such methods are described by Edberg in U.S. Pat. No. 4,925,789.

Currently Available Detection Methods

The two standard and widely accepted procedures for evaluating the presence of microorganisms in drinking water include the multiple tube fermentation coupled with most probable number analysis (MPN) test and the membrane filtration (MF) test. The protocol for these methods for detecting coliform bacteria involve presumptive tests coupled with confirmation tests which take some 48 to 96 hours to complete. Also, the results of these tests are complicated by the presence of non-coliform bacteria which can, if present at greater than 500 microorganisms per milliliter, cause false positive or false negative readings.

The invention of the COLILERT® test, described in Edberg, U.S. Pat. No. 4,925,789, constituted a tremendous advancement over the previously available methods. Using that method, it is possible to detect coliforms in samples in concentrations as low as one microorganism per 100 milliliters of sample. It features a combination of the presumptive step and the confirmatory step for microbial identification. Therefore, the speed of detection is much faster, and the chances of obtaining false negative or false positive readings are much reduced since various selective agents are present in the medium which greatly restrict the growth of non-coliform bacteria. The media of the present invention, however, contemplate using at least a two fold increase in the concentration of amino acids, vitamins, trace elements and salts over the previously used media. Surprisingly, this change in the medium produces a much more rapid detection without loss of specificity.

The present invention was compared to existing methods for detecting coliforms and E. coli in samples.

Detection Methods

The number of target microbes present in a liquid sample may be quantified by mixing a liquid sample with the medium described above, placing the liquid sample including the medium in suitable containers for incubation, incubating the liquid sample and medium mixture, observing the quantity and quality of a detectable characteristic signal, and comparing the quantity and quality of a detectable characteristic signal with most probable number values. This quantifying process features comparing the quantity and quality of the characteristic which has been altered, preferably a color change, to most probable number values obtained from samples where the concentration and characteristic change have been correlated with samples for which bacterial concentration is known. See e.g., *Compendium of Methods for the Microbiological Examination of Foods* 3rd ed., Edited by Vanderzant and Splittstoesser, 1992. The most probable number technique allows estimates of bacterial concentrations that are below detectable limits of other methods. The most probable number is estimated from responses where the results are reported as positive or negative in one or more dilutions of the sample. The method requires that not all samples provide a positive result and usually at least three samples of each dilution are required. Many most probable number charts are available. One such series is provided by de Man, *Eur. J. Appl. Microbiol.* 1:67 (1975) herein incorporated by reference. Estimates of the most probable number may be made using the general formula reported by Thomas, *J. Am. Water Works Assoc.* 34:572 (1942) as follows:

$$MPN/g = P/(NT)$$

where P is the number of positive tibes, N is the total quantity of sample in all negative tubes, and T is the total quantity of sample in all tubes. The quantities are reported in terms of grams.

Naqui et al. in patent application, U.S. Ser. No. 08/201,110, filed Feb. 23, 1994 now U.S. Pat. No. 5,518,892 herein incorporated by reference, describes an accurate method for quantifying the number of bacteria in a liquid sample. The invention employs a novel apparatus for holding a liquid sample. The apparatus features a bag which is designed for receiving a liquid sample and subsequently distributes the liquid sample into separate compartments within the bag so that different aliquots of one or more sizes may be tested. The invention described in that application further allows quantifying the microorganisms present in the sample by adding a medium to promote growth of microorganisms, heat sealing the bag of the invention for about five seconds at a temperature of about 250° F. to 350° F., incubating the sample at an appropriate temperature for an appropriate length of time to allow growth of microorganisms, and recording and analyzing the results. The quantifying step involves detecting the quantity and quality of the color change, and comparing that quantity and quality with results obtained for a series of samples for which the concentration of total viable bacteria was known.

Experiment 1
Injured Organisms Protocol

The following protocol follows the U.S. EPA procedures. The procedure was followed for collecting samples of injured microorganisms. It is provided as a means for insuring proper sampling and care of samples to be used in comparisons of the specificity and time required for a result for the media of this invention and prior art media.

1. Obtain 2 liters of fresh primary sewage effluent from an outside source (e.g., waste water treatment facility).
2. Pass the effluent through a Whatman-40 (150 mm diameter) filter.
3. Let filtrate reach room temperature prior to chlorine injuring.
4. Check pH and temperature of effluent then dispense 49.5 ml aliquots into 21 polystyrene vessels that do not contain sodium thiosulfate.
5. Shake the samples on a Roto-Mix 50800 platform (setting 2) at room temperature.
6. Aliquot NaOCl (sodium hypochloride) solution (5 to 6% into each sample at a final concentration of 5 ppm. Immediately check total and free chlorine levels of one sample.
7. Add 25 µl of a 10% solution of sodium thiosulfate to the first sample after 2 minutes. Add the same amount of sodium thiosulfate to the remaining samples at 2 minute intervals after the first addition.
8. Measure the total and free chlorine concentration at the midpoint of injuring and in the last sample, just prior to the addition of sodium thiosulfate.
9. Determine the number of surviving coliforms in each sample by membrane filtration onto mEndo plates, and determine the original concentration of coliforms in the untreated effluent by membrane filtration (dilutions required) onto mEndo plates.
10. Count the number of coliforms on each mEndo plate (a selective medium for *E. coli*) after 22 to 24 hours of incubation. Choose the appropriate sample which has suffered a 2 Log 10 to 4 Log 10 reduction in total coliform concentration and prepare a series of two fold dilutions of this sample. The number of dilutions performed depends on the number of surviving coliforms present and must allow for at least two dilutions which contain no coliforms.

Detecting the Presence or Absence of Injured Organisms

This experiment is designed to compare the relative performance of Medium 2 and Colilert® medium in detecting the presence of injured coliforms and *E. coli* from chlorinated primary sewage effluent. The procedure followed to compare the two media included first inoculating each diluted chlorinated effluent sample into the test medium with 1 ml of each dilution into 3 Colilert® tests and 1 ml of each dilution into 3 Medium 2 tests. Next, the Medium 2 tests were thermally equilibrated for 20 minutes in a 35° C.±0.5° C. water bath and the other tests placed in a 35° C. ±0.5° C. dry incubator. After 20 minutes, the Medium 2 tests were placed in the 35° C. dry incubator. Color and fluorescence were then monitored and results recorded at 18 hours for Medium 2 and at 24 hours for Colilert® medium. Random positive Medium 2 samples were streaked onto EMB agar for isolation and further identification using API 20E.

RESULTS

Seven effluents from four separate geographically diverse sites in Georgia, Maine, Connecticut and California were used in these studies. A total of 201 Medium 2 and 201 Colilert® vessels were inoculated with the treated effluent dilutions. The following results were obtained:

| Test | Time | # of Coliform positive | # of *E. coli* positive |
| --- | --- | --- | --- |
| Medium 2 | 18 hrs | 91 | 6 |
| Colilert | 24 hrs | 92 | 5 |

An analysis by the Chi-square test indicated that these values were not significantly different within a 95% confidence index. A total of 43 positive Medium 2 samples were speciated using the API 20E kit and all 43 samples contained coliform bacteria. These data show that Medium 2, after 18 hours of incubation, detected a similar number of injured coliforms and *E. coli* as Colilert® medium after 24 hours of incubation. The medium of this invention is, therefore, as specific as the Colilert® medium, and it allows detection of microorganisms in 18 hours while the Colilert® medium allows detection in 24 hours.

Experiment 2
Injured Organisms MPN Method vs LTB Method

This experiment is designed to compare the performance of Medium 2 to the Lauryl Tryptose Broth (LTB) (EPA reference) method in detecting the presence of injured coliforms and E. coli from chlorinated primary sewage effluent. Test results were obtained by first inoculating each diluted sample into the test medium by adding 100 µl of each dilution into 10 Medium 2 tubes (10 ml each) and 100 µl of each dilution into 10 LTB tubes (1× concentration). Next, the Medium 2 tests were thermally equilibrated for 20 minutes in a 35° C. water bath. The LTB tubes were placed directly into the 35° C. dry incubator. After 20 minutes, the Medium 2 tests were placed in the 35° C. dry incubator. Color and fluorescence were then monitored and the results recorded at 18 hours for Medium 2. Random positive Medium 2 samples were streaked onto EMB agar for isolation and further identification using API 20E. The LTB samples were then checked for the presence of gas after 24 and 48 hours of incubation. If gas was present, the samples were inoculated into 10 ml of BGLB (Brilliant Green Lactose Broth) and 10 ml of E. coli and 4-methylumbelliferone glucuronide broth (EC-MUG). The BGLB tubes were incubated in a 35° C. dry incubator for between 24 and 48 hours. The EC-MUG tubes were incubated in a 44.5° C. water bath for 24 hours. The presence of gas in the BGLB tubes indicates the presence of coliforms. The presence of gas and fluorescence in the EC-MUG tubes indicate the presence of E. coli. The experiment is complete after the BGLB and EC-MUG tubes have finished incubating.

RESULTS

Two effluents from two primary sewage effluent sites in Maine and California were used in this study. A total of 240 Medium 2 MPN tubes were compared against 240 LTB tubes. The results are as follows:

| Test | Time | # of Coliform positive | # of E. coli positive |
| --- | --- | --- | --- |
| Medium 2 | 18 hrs | 104 | 33 |
| LTB method | 96 hrs | 75 | 16 |

An analysis by the Chi-square test indicated that these values were significantly different within a 95% confidence index. A total of 46 positive Medium 2 samples were speciated using the API 20E kit and all 46 samples contained coliform bacteria. Therefore, Medium 2 is better than the LTB method in recovering injured coliforms and E. coli from primary sewage effluent.

Experiment 3
Heterotrophic Interference

This experiment was designed to test the performance of Medium 2 and Colilert® medium in detecting non-injured coliforms and E. coli in the presence of a high concentration of heterotrophic bacteria. The following procedure was followed. First, each 100 ml Medium 2 and Colilert® test vessel was inoculated with 1 to 10 CFU of the following bacteria: *Escherichia coli* ATCC 25922, *Citrobacter freundii* ATCC 8090, *Klebsiella pneumoniae* ATCC 13883, and *Enterobacter cloacae* ATCC 33457. This step was then repeated with a second set of samples. *Aeromonas hydrophilia* ATCC 35654, *Pseudomonas aeruginosa* (ATCC 10145) or *Pseudomonas putrefaciens* (a natural isolate) was inoculated into the second set of vessels at a concentration range of 16,000 to 10,000 CFU/ml. Medium 2 and Colilert® test vessels were inoculated with *A. hydrophilia, Pseudomonas aeruginosa* or *P. putrefaciens* alone to test for false positive results. The Medium 2 tests were thermally equilibrated for 20 minutes in a 35° C. waterbath and the Colilert® tests placed in a 35° C. dry incubator. After 20 minutes, the Medium 2 tests were placed in the 35° C. dry incubator. Color and fluorescence were then monitored and results recorded at 18 hours for Medium 2 and at 24 hours for Colilert®.

RESULTS

The following results were obtained:
Coliforms with and without Heterotrophic Bacteria

| Test | Incubation Time | # of Coliform positive[a] | # of E. coli positive[b] |
| --- | --- | --- | --- |
| Medium 2 | 18 hrs | 33 | 9 |
| Colilert ® | 24 hrs | 33 | 6 |

A total of 36 Medium 2 and 36 Colilert tests were performed in this study. Nine out of each set of 36 tests contained E. Coli.

| | Heterotrophic Bacteria Only | | |
| --- | --- | --- | --- |
| Test | Incubation Time | # of Coliform positive | # of E. coli positive |
| Medium 2 | 18 hrs | 0 | 0 |
| Colilert ® | 24 hrs | 0 | 0 |

A total of 24 Medium 2 and 24 Colilert tests were carried out in this study.

Other embodiments are within the following claims.

What is claimed is:

1. A target microbe-specific medium which allows the detection of the presence or absence of a target microbe in a liquified environmental or biological sample comprising:

a) an effective amount of vitamin, amino acid, element and salt ingredients operable to allow viability and reproduction of said target microbe at a rate such that any detectable change in said sample observable within 18 hours for a sample with less than 10 target microbes per 100 ml; and b) an effective amount of one or more nutrient-indicators provided in an amount sufficient to produce a detectable characteristic signal in the medium during growth of the target microbe; and said nutrient-indicator being operable to alter a detectable characteristic of the sample if metabolized by the target microbe so as to confirm the presence or absence of the target microbe in the sample.

2. The target microbe-specific medium of claim 1 wherein said nutrient indicator alters the color of said target microbe-specific medium.

3. The target microbe-specific medium of claim 2 wherein said nutrient indicator alters the color of said target microbe-specific medium in the visible wavelength range.

4. The target microbe-specific medium of claim 2 wherein said nutrient indicator comprises a moiety capable of fluorescing and detectable in a wavelength range visible after exposure to an excitation light source.

5. The target microbe-specific medium of claim 1 wherein said target microbe is a coliform.

6. The target microbe-specific medium of claim 5 wherein said coliform is *E. coli*.

7. The target microbe-specific medium of claim 1 wherein said nutrient indicator is a β-D-glucuronidase substrate.

8. The target microbe-specific medium of claim 7 wherein said β-D-glucuronidase substrate is selected from the group consisting of orthonitrophenyl-β-D-glucuronide, β-naphthalamide-β-D-glucuronide, α-naphthol-β-D-glucuronide, and 4-methylumbelliferyl-β-D-glucuronide.

9. The target microbe-specific medium of claim 1 wherein said nutrient indicator is a β-D-galactosidase substrate.

10. The target microbe-specific medium of claim 9 wherein said β-D-galactosidase substrate is selected from the group consisting of orthonitrophenyl-β-D-galactopyranoside and 4-methylumbelliferyl-β-D-galactopyranoside.

11. The target microbe-specific medium of claim 1 wherein said nutrient indicator is a β-glucosidase substrate.

12. The target microbe-specific medium of claim 1 wherein said nutrient indicator is a L-pyronidonyl aminopeptidase substrate.

13. The target microbe-specific medium of claim 1 wherein said nutrient indicator is a L-alanine aminopeptidase substrate.

14. The target microbe-specific medium of claim 1 further comprising an antibiotic which prevents non-target microbes from metabolizing said nutrient indicator.

15. The target microbe-specific medium of claim 14 wherein said antibiotic operates against gram positive microbes or non-target gram negative microbes.

16. The target microbe-specific medium of claim 1 wherein said medium is a non-sterile, water soluble powder.

17. The target microbe-specific medium of claim 1 further comprising an amount of sodium pyruvate sufficient to assist the recovery of metabolically injured cells.

18. The target microbe-specific medium of claim 1 comprising effective amounts of some or all of the following ingredients to allow detection of coliforms in a liquid sample 18 hours:

a) Nitrogen;
b) Amino acids necessary for or conducive to microbe growth selected from the group consisting of Alanine, Arginine, Aspartic Acid, Cystine, Glutamic Acid, Glycine, Histidine, Isoleucine, Leucine, Lysine, Methionine, Phenylalanine, Proline, Serine, Threonine, Tryptophan, Tyrosine, and Valine;
c) Elements selected from the group consisting of Calcium, Chloride, Cobalt, Copper, Iron, Lead, Magnesium, Manganese, Phosphate, Potassium, Sodium, Sulfate, Sulfur, Tin, Zinc, Biotin, Choline, Folic Acid, Inositol, Nicotinic Acid, PABA, Pantothenic Acid, Pyridoxine, Riboflavin, Thiamine, and Thymidine;
d) Vitamins selected from the group consisting of Biotin, Choline, Cyanocobalamin, Folic Acid, Inositol, Nicotinic Acid, PABA, Pantothenic Acid, Pyridoxine, Riboflavin, Thiamine, Niacin and Thymidine;
e) one or more inducers of enzyme activity;
f) one or more nutrient indicators; and
g) one or more precursors of amino acids or DNA.

19. A medium comprising 4.5 to 5.5 g/liter ammonium sulfate or an equivalent amount of ammonium ions, one or more buffers in an amount equivalent to 6.0 to 7.5 g/liter HEPES free acid, 4.7 to 5.8 g/liter HEPES sodium salt, 0.12 to 0.17 g/liter D-gluconic acid, 0.036 to 0.044 g/liter sodium sulfite or an eouivalent source of sulfite ions, 0.001 to 0.003 g/liter amphotericin B or an equivalently effective amount of an antifungal agent, 0.09 to 0.11 g/liter magnesium sulfate or an equivalent source of magnesium ions, 0.450 to 0.550 g/liter ONPG or an equivalent amount of a nutrient indicator, 0.05 to 0.10 g/liter MUG or an equivalent amount of a nutrient indicator, 0.0004 to 0.0006 g/liter zinc sulfate (heptahydrate) or an equivalent source of zinc ions, and 0.0004 to 0.0006 g/liter manganese sulfate or an equivalent source of manganese ions; Alanine at least 0.025 g/liter, Arginine at least 0.030 g/liter, Aspartic Acid at least 0.056 g/liter, Glutamic Acid at least 0.1021 g/liter, Glycine at least 0.015 g/liter, Cystine at least 0.002 g/liter, Histidine at least 0.0058 g/liter, Isoleucine at least 0.0145 g/liter, Leucine at least 0.0301 g/liter, Lysine at least 0.0342 g/liter, Methionine at least 0.0119 g/liter, Phenylalanine at least 0.0181 g/liter, Serine at least 0.0287 g/liter, Threonine at least 0.0181 g/liter, Tryptophan at least 0.0036 g/liter, Tyrosine at least 0.0064 g/liter, and Valine at least 0.0235 g/liter; and Iron (at least 0.00165 mg/l) Calcium, Phosphate, Potassium, Sodium, Chloride, Cobalt, Copper, Lead and Manganese; and Biotin at least 0.0005 mg/l, Choline at least 0.05 mg/l, Folic Acid at least 0.00075 mg/l, Inositol at least 0.06 mg/l, Niacin at least 0.00385 mg/l, PABA at least 0.020 mg/l, Pantothenic Acid at least 0.01095 mg/l, Pyridoxine at least 0.0015 mg/l, Riboflavin at least 0.0028 mg/l, Thiamine at least 0.0037 mg/l, Thymidine at least 0.010 mg/l, and Cyanocobalamin in trace amounts.

20. A target microbe specific medium comprising:

a) 4.5 to 5.5 g/liter ammonium sulfate or an equivalent amount of ammonium ions, one or more buffers in amounts equivalent to 6.0 to 7.5 g/liter HEPES free acid and 4.7 to 5.8 g/liter HEPES sodium salt, 0.13 to 0.16 g/liter D-gluconic acid, 0.036 to 0.044 g/liter sodium sulfite or an equivalent amount of sulfite ions, 0.0009 to 0.0011 g/liter amphotericin B or an equivalently effective amount of antifungal agent, 0.09 to 0.11 g/liter magnesium sulfate or an equivalent amount of magnesium ions, one or more nutrient indicators in amounts equivalent to 0.450 to 0.550 g/liter orthonitrophenyl-β-D-galactopyranoside (ONPG) or 0.05 to 0.10 g/liter 4-methylumbelliferyl-β-D-glucuronide (MUG)), 0.0004 to 0.0006 g/liter zinc sulfate or an equivalent amount of zinc ions, and 0.0004 to 0.0006 g/liter manganese sulfate or an equivalent amount of manganese ions, a nitrogen content of at least 1.1 to 1.7 g/liter; and b) amino acids required for growth of the target microbe, in effective amounts to promote growth, selected from the group consisting of: Alanine, Arginine, Aspartic Acid, Glutamic Acid, Glycine, Proline, Cystine, Histidine, Isoleucine, Leucine, Lysine, Methionine, Phenylalanine, Serine, Threonine, Tryptophan, Tyrosine, and Valine; and c) one or more agents in amounts sufficient to aid growth of microbes selected from the group consisting of: Iron (at least 0.00165 mg/l), Calcium, Phosphate, Potassium, Sodium, Chloride, Cobalt, Copper, Lead and Manganese; and d) one or more vitamins in amounts sufficient to aid growth of microbes selected from the group consisting of: Biotin, Choline, Cyanocobalamin, Folic Acid, Inositol, Nicotinic Acid, Niacin, PABA, Pantothenic Acid, Pyridoxine, Riboflavin, Thiamine, and Thymidine; and e) one or more agents active to inhibit growth of non-coliform microbes.

21. A method for detecting the presence or absence of a target microbe in an environmental or biological liquid sample comprising the step of thermally equilibrating said liquid sample with a target microbe-specific detection medium having a nutrient indicator operable to alter a detectable characteristic of the sample if said target microbe is present in said sample to incubation temperature in a water bath prior to placing said liquid sample in a dry incubator and monitoring the sample to determine whether said detectable characteristic is altered.

22. The method of claim 21 wherein said incubation temperature is 30° to 41° C. and is maintained for more than 10 minutes.

23. A method for detecting the presence or absence of a target microbe in an environmental or biological liquid sample within 18 hours comprising the steps of:

a) mixing said liquid sample with a medium which includes an effective amount of via, amino acid, element and salt ingredients operable to allow viability and reproduction of said target microbe in the presence of a nutrient-indicator; and an effective amount of a nutrient-indicator which is provided in an amount sufficient to support growth of said target organism until a detectable characteristic signal is produced in the medium during growth; and said nutrient-indicator being operable to alter a detectable characteristic of the sample if metabolized by the target microbe so as to cinform the presence or absence of the target microbe in the sample;

b) warming said liquid sample and medium mixture to an incubation temperature of 30° to 41° C. and said liquid sample is maintained at said incubation temperature for 10 minutes or more; and c) monitoring the sample to determine whether said detectable characteristic has been altered.

24. The method of claim 23 wherein said medium further comprises an effective amount of at least one antibiotic which inhibits growth of one or more potential non-target microbes.

25. The method of claim 23 wherein said medium comprises:

a) Nitrogen;

b) Amino acids necessary for or conducive to microbe growth selected from the group consisting of Alanine, Arginine, Aspartic Acid, Cystine, Glutamic Acid, Glycine, Histidine, Isoleucine, Leucine, Lysine, Methionine, Phenylalanine, Proline, Serine, Threonine, Tryptophan, Tyrosine, and Valine;

c) Elements selected from the group consisting of Calcium, Chloride, Cobalt, Copper, Iron, Lead, Magnesium, Manganese, Phosphate, Potassium, Sodium, Sulfate, Sulfur, Tin, Zinc, Biotin, Choline, Folic Acid, Inositol, Nicotinic Acid, PABA, Pantothenic Acid, Pyridoxine, Riboflavin, Thiamine, and Thymidine;

d) Vitamins selected from the group consisting of Biotin, Folic Acid, Pyridoxine, Riboflavin, Thiamine, Vitamin B12, Niacin and Pantothenic Acid;

e) one or more inducers of enzyme activity;

f) one or more nutrient indicators; and g) one or more precursors of amino acids or DNA.

26. The method of claim 23 wherein said medium comprises:

a) 4.5 to 5.5 g/liter ammonium sulfate, one or more buffers in amounts equivalent to 6.0 to 7.5 g/liter HEPES free acid and 4.7 to 5.8 g/liter HEPES sodium salt, 0.13 to 0.16 g/liter D-gluconic acid, 0.036 to 0.044 g/liter sodium sulfite, 0.0009 to 0.0011 g/liter amphotericin B, 0.09 to 0.11 g/liter magnesium sulfate, one or more nutrient indicators in amounts equivalent to 0.450 to 0.550 g/liter ortho-nitrophenyl-$\beta$-D-galactopyranoside (ONPG) or 0.05 to 0.10 g/liter 4-methylumbelliferyl-$\beta$-D-glucuronide (MUG)), 0.0004 to 0.0006 g/liter zinc sulfate, and 0.0004 to 0.0006 g/liter manganese sulfate, a nitrogen content of at least 1.1 to 1.7 g/liter including an amino nitrogen content of at least 0.06 g/liter; and b) amino acids required for growth of the target microbe, in effective amounts to promote growth, selected from the group consisting of: Alanine, Arginine, Aspartic Acid, Glutamic Acid, Glycine, Proline, Cystine, Histidine, Isoleucine, Leucine, Lysine, Methionine, Phenylalanine, Serine, Threonine, Tryptophan, Tyrosine, and Valine; and c) one or more agents in amounts sufficient to aid growth of microbes selected from the group consisting of: Iron (at least 0.00165 mg/l), Calcium (at least 0.0003 g/liter), Phosphate (at least 0.0005 g/liter), Potassium (at least 0.004 g/liter), Sodium (at least 0.03 g/liter), Chloride, Cobalt, Copper, Lead and Manganese; and d) one or more vitamins in amounts sufficient to aid growth of microbes selected from the group consisting of: Biotin, Choline, Cyanocobalamin, Folic Acid, Inositol, Nicotinic Acid, Niacin, PABA, Pantothenic Acid, Pyridoxine, Riboflavin, Thiamine, and Thymidine; and e) one or more agents active to inhibit growth of non-coliform microbes.

27. A method for detecting the presence or absence of a target microbe in an environmental or biological liquid sample comprising the steps of mixing a target microbe specific medium of any of claims 1–20 with said liquid sample to form a liquid mixture, and incubating the mixture at a temperature sufficient to allow detection of said target microbe in 18 hours when said sample has less than 10 target microbes per 100 ml.

* * * * *

UNITED STATES PATENT AND TRADEMARK OFFICE
CERTIFICATE OF CORRECTION

PATENT NO. : 5,610,029

DATED : March 11, 1997

INVENTOR(S) :

Elizabeth Ehrenfeld et al.

It is certified that error appears in the above-identified patent and that said Letters Patent is hereby corrected as shown below:

Column 16, Line 43: Insert --is-- before the word "observable."

Column 17, Line 35: changing "within" to --in--.

Signed and Sealed this

Sixteenth Day of February, 1999

Attest:

Attesting Officer

*Acting Commissioner of Patents and Trademarks*